(12) United States Patent
Al Ali et al.

(10) Patent No.: US 11,497,714 B2
(45) Date of Patent: *Nov. 15, 2022

(54) NANO-CARRIER TOPICAL COMPOSITION WITH VITAMIN D3

(71) Applicants: Sadat A. Al Ali, Lombard, IL (US); Haifa A. Al-Turki, Alkhobar (SA)

(72) Inventors: Sadat A. Al Ali, Lombard, IL (US); Haifa A. Al-Turki, Alkhobar (SA)

(*) Notice: Subject to any disclaimer, the term of this patent is extended or adjusted under 35 U.S.C. 154(b) by 0 days.

This patent is subject to a terminal disclaimer.

(21) Appl. No.: 17/064,555

(22) Filed: Oct. 6, 2020

(65) Prior Publication Data

US 2022/0105036 A1 Apr. 7, 2022

(51) Int. Cl.
| | |
|---|---|
| *A61K 9/107* | (2006.01) |
| *A61K 31/593* | (2006.01) |
| *A61K 9/00* | (2006.01) |
| *A61K 47/26* | (2006.01) |
| *A61K 47/28* | (2006.01) |

(Continued)

(52) U.S. Cl.
CPC .......... *A61K 9/1075* (2013.01); *A61K 9/0014* (2013.01); *A61K 31/593* (2013.01); *A61K 47/02* (2013.01); *A61K 47/10* (2013.01); *A61K 47/14* (2013.01); *A61K 47/183* (2013.01);

(Continued)

(58) Field of Classification Search
CPC ...... A61K 9/1075; A61K 47/14; A61K 47/26; A61K 47/44; A61K 47/183; A61K 9/0014; A61K 47/28; A61K 31/593; A61K 47/02; A61K 47/10; A61K 47/34
See application file for complete search history.

(56) References Cited

U.S. PATENT DOCUMENTS

| | | |
|---|---|---|
| 9,707,243 B2 | 7/2017 | Ali |
| 2003/0180347 A1 | 9/2003 | Young et al. |

(Continued)

FOREIGN PATENT DOCUMENTS

| | | |
|---|---|---|
| GB | 799902 A | 8/1958 |
| GB | 1453239 A | 10/1976 |

(Continued)

OTHER PUBLICATIONS

Kim et al. (WO 2010090502 A2) Machine Translation (Year: 2010).*

*Primary Examiner* — Robert A Wax
*Assistant Examiner* — Quanglong N Truong
(74) *Attorney, Agent, or Firm* — Nath, Goldberg & Meyer; Richard C. Litman

(57) ABSTRACT

The nano-carrier topical composition with Vitamin D3 includes Vitamin D3, Span 40, Span 80, cholesterol, ethanol, almond oil, glycerin, water, aloe vera gel, and sodium hydroxide. The nano-carrier topical composition with Vitamin D3 forms an alkaline composition having nano-carriers with an average diameter of 50.8 μm. The composition can be transported through the stratum corneum so that the composition may be used for fulfilling daily requirements for Vitamin D3, treatment of bone conditions, such as rickets and osteomalacia, and supportive therapy in osteopenia and osteoporosis. Optionally, the composition may include perfume and/or one or more preservatives (e.g., a carbomer, methyl paraben, EDTA, or the like), or other additives that do not affect the active ingredients. The composition is preferably formulated as a cream or emulsion wherein the nano-carriers are niosomes.

10 Claims, 2 Drawing Sheets

(51) Int. Cl.
*A61K 47/34* (2017.01)
*A61K 47/44* (2017.01)
*A61K 47/02* (2006.01)
*A61K 47/14* (2017.01)
*A61K 47/18* (2017.01)
*A61K 47/10* (2017.01)

(52) U.S. Cl.
CPC .............. *A61K 47/26* (2013.01); *A61K 47/28* (2013.01); *A61K 47/34* (2013.01); *A61K 47/44* (2013.01)

(56) References Cited

U.S. PATENT DOCUMENTS

| | | |
|---|---|---|
| 2010/0081637 A1 | 4/2010 | Strube |
| 2016/0235770 A1 | 8/2016 | Clagett-Dame et al. |
| 2016/0375040 A1* | 12/2016 | Ali .................... A61K 36/53 |
| | | 514/167 |

FOREIGN PATENT DOCUMENTS

| | | |
|---|---|---|
| GB | 2527726 A | 1/2016 |
| WO | 2017156608 A1 | 9/2017 |
| WO | 2019030772 A1 | 2/2019 |

\* cited by examiner

NANO-CARRIER TOPICAL COMPOSITION WITH VITAMIN D3

BACKGROUND

1. Field

The disclosure of the present patent application relates to improved Vitamin D supplements, and particularly to a nano-carrier topical composition formulated for transdermal delivery of Vitamin D3 to a patient in need thereof, e.g., patients with rickets, osteomalacia, osteopenia, osteoporosis, or other malabsorption conditions.

2. Description of the Related Art

Two principle types of Vitamin D include Vitamin D2 and D3. Vitamin D2 (ergocalciferol) is derived from such sources as fortified milk, herring, mackerel, tuna, salmon, sardines, eggs, fortified cereals, and baked goods. Vitamin D3 (cholecalciferol) is a pro-hormone and an essential nutrient produced in the skin with exposure to UV rays, consumption of animal products and fortified foods. Vitamin D3 can be produced photochemically by the action of sunlight or ultraviolet light from the precursor sterol 7-dehydrocholesterol, which is present in the epidermis or skin. Vitamin D3 can also be consumed in the form of fish oil or foods, such as eggs or fish. Analogs of Vitamin D may be produced synthetically.

Vitamin D2 and Vitamin D3 are subsequently 25-hydroxylated in the liver to form 25-hydroxyvitamin D2 (25OHD2) and 25-hydroxyvitamin D3 (25OHD3), respectively. 25OHD2 and 25OHD3 represent the main body reservoir and transport form of vitamin D and are stored in adipose tissue or are tightly bound by a transport protein while in circulation.

The exact levels of 25OHD2 and 25OHD3 that reflect optimal body stores are uncertain. Mild to modest deficiency can be associated with osteoporosis or secondary hyperparathyroidism. Severe deficiency may lead to failure to mineralize newly formed osteoid in bone, resulting in rickets in children and osteomalacia in adults.

Deficiency of Vitamin D is generally due to inadequate exposure to the sun or due to its low content in the diet. As early as the 1980's, it was found that the ethnic Saudi population has low Vitamin D. Extensive studies have shown that deficiency exists not only in the winter, but also in the summer months due to non-exposure to the sun. It has been found in the healthy Saudi population that Vitamin D deficiency exists in about 40-60% of men and women over 50 years of age. Recent studies put the deficiency of Vitamin D at 95-100%.

For any drug, large proportions of oral prescriptions are never taken at all. Recent estimates for noncompliance range from study to study, with ranges of 62 to 84 percent using electronic monitoring. In other words, many do not comply with the recommended dosages of oral prescriptions.

Conventional routes of administration of Vitamin D include oral or injectable administration. For oral Vitamin D and calcium supplementation, the compliance is reported between 20-60%. It has been reported that at the end of 3 months, only 23.8% of patients were taking the supplementation and another 26.2% were partially compliant. Physicians attempted to address this problem by prescribing monthly, quarterly and yearly dosages. A yearly oral dose of 500,000 international units was found to result in an increased risk of falls and fractures. Recently, quarterly dosages of 150,000 IU of Vitamin D and intermittent large doses of vitamin D have been found to be ineffective.

Deficiency of Vitamin D is often significant in those who are non-compliant, i.e., those who fail to take prescribed dosages of oral Vitamin D. Typically, non-compliance is associated with patients who are already required to take a number of other oral medications. It was reported that between 40-45% of patients become non-compliant within six months of initiating therapy for osteopenia and osteoporosis. It was found that about 12% of elderly U.S. patients take ≥12 medications and 23% take at least 5 prescription medications. Requiring additional oral medications becomes burdensome for such patients. As Vitamin D is an essential part of osteopenia and osteoporosis treatment, a suitable alternative is desirable. An alternative to oral supplementation would likely increase compliance of patients already burdened with other oral medications.

Recently, topical products for administering vitamin D3 have been developed, such as those disclosed in U.S. Pat. No. 9,707,243 B2. This patent teaches topical compositions with Vitamin D3 having Vitamin D3, one or more aromatic oils, and aloe vera gel for use in treatment of bone conditions. These topical compositions are generally formulated as a gel. One challenge for topical compositions, such as the compositions taught in U.S. Pat. No. 9,707,243, is successfully delivering a sufficient dose of Vitamin D3 transdermally in order to restore normal Vitamin D3 levels. Another challenge is reliably delivering a sufficient dose in people with different skin conditions and different skin pore sizes.

Thus, a nano-carrier topical composition with vitamin D3 solving the aforementioned problems is desired.

SUMMARY

The nano-carrier topical composition with Vitamin D3 includes Vitamin D3, Span™ 40, Span™ 80, cholesterol, ethanol, glycerin, water, almond oil, sodium hydroxide, and aloe vera gel. Vitamin D3 is soluble in aromatic oils. Aloe vera gel enables transport through the stratum corneum so that the composition may be used for treatment of bone conditions, such as rickets, osteomalacia, osteopenia, osteoporosis, and other malabsorption associated conditions. The composition may be formulated as a cream or emulsion. The composition includes nano-carriers, e.g., niosomes, in order to enhance delivery of vitamin D3.

The nano-carrier topical composition with Vitamin D3 may be applied topically to deliver Vitamin D3 to a human subject. Vitamin D3 may cross the skin barrier and pass into the body's systemic circulation once the nano-carrier topical composition with Vitamin D3 is applied to the skin.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
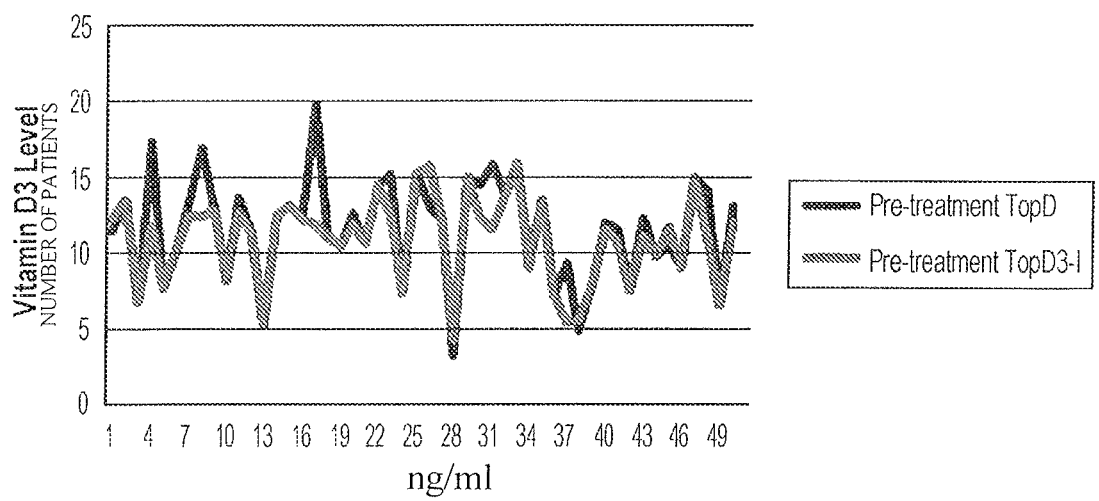
FIG. 1 depicts a graph comparing the pre-treatment vitamin D3 levels of patients allocated to the TopD3 group (Group A) and patients allocated to the TopD3-I group (Group B).

A nano-carrier topical composition with Vitamin D3 includes Vitamin D3, Span™ 40, Span™ 80, cholesterol, ethanol, glycerin, water, almond oil, sodium hydroxide, and aloe vera gel. Vitamin D3 is soluble in aromatic oils. Aloe vera gel enables transport through the stratum corneum so that the composition may be used for treatment of bone conditions, such as rickets, osteomalacia, osteopenia, osteoporosis, and other malabsorption associated conditions. The composition may be formulated as a cream or emulsion. Preferably, the composition includes nano-carriers, e.g., niosomes, to enhance delivery of vitamin D3.

The nano-carrier topical composition with Vitamin D3 may be applied topically to deliver Vitamin D3 to a human subject. Vitamin D3 may cross the skin barrier and pass into the body's systemic circulation once the topical composition with Vitamin D3 is applied to the skin.

The skin is composed of two primary layers, the epidermis on the outside and the dermis on the inside. The stratum corneum is the outermost layer of the epidermis, consisting of dead cells. The stratum corneum forms a barrier to protect underlying tissue from infection, dehydration, chemicals and mechanical stress. Although the stratum corneum is an efficient barrier, the topical composition with Vitamin D3 is able to penetrate the stratum corneum and reach the underlying tissues and blood vessels. Accordingly, the nano-carrier topical composition with Vitamin D3 may provide a suitable alternative to oral Vitamin D supplements.

One route that the nano-carrier topical composition with Vitamin D3 may take to penetrate the stratum corneum would be through pores, or natural openings in the skin. The average human skin pore diameter is reported to range between 250 μm and 500 μm. Thus, traditional topical Vitamin D3 compositions, such as the composition taught by U.S. Pat. No. 9,707,243 may not be able to take advantage of skin pores in order to quickly cross the stratum corneum due to their larger size (the composition taught by U.S. Pat. No. 9,707,243 produced micelles having an average diameter of 312.7 μm, as discussed in the Example below). In contrast, the nano-carrier topical composition with Vitamin D3 includes nano-carriers with an average diameter of 50.8 μm, allowing the nano-carrier topical composition to quickly cross the stratum corneum via skin pores. The nano-carrier topical composition with Vitamin D3 has an alkaline pH, further increasing its absorption through human skin.

The term composition, as used herein, may refer to a combination of ingredients to form a lotion, gel, cream, ointment, paste, foam, aerosol spray, and the like. Topical, as used herein, may refer to application of a substance to a specific area of the skin. About, as used herein, may refer to any value within 10% of the numerical value modified by the term "about".

The nano-carrier topical composition with Vitamin D3 includes Span™ 40 (sorbitan monopalmitate) and Span™ 80 (sorbitan oleate). Span™ 40 and Span™ 80 are nonionic surfactants which may operate as emulsifiers. Thus, Span™ 40 and Span™80 may enhance dispersion of the various components within the micellar topical composition and thereby enhance skin penetration.

The nano-carrier topical composition with Vitamin D3 includes cholesterol, which may serve as an emollient.

The nano-carrier topical composition includes Vitamin D3. Preferably, the composition is formulated to deliver 5000 IU of Vitamin D3 in 1 ml (gram) of gel.

The nano-carrier topical composition with Vitamin D3 includes aloe vera gel. Aloe vera is a succulent plant species. The long, green leaves of the aloe vera plant contain aloe vera gel. Aloe vera gel is typically used for manufacture of topical-like ointments and gel preparations. It has been found that aloe vera gel has the ability to improve the bioavailability of co-administered vitamins in human subjects. Aloe vera gel may also enhance skin penetration of the topical composition with Vitamin D3. The nano-carrier topical composition with Vitamin D3 may include one or more other plant extracts from succulent plants to enhance skin penetration, including, but not limited to, cacti and seaweed extract.

The nano-carrier topical composition with Vitamin D3 includes almond oil. Vitamin D is a fat-soluble vitamin that dissolves easily in aromatic oils. Almond oil may be 100% pure oil from the almond (*Prunus dulcis*).

The nano-carrier topical composition with Vitamin D3 includes glycerin. Glycerin is a humectant, i.e., it absorbs ambient water. Glycerin may also enhance penetration of the topical composition with Vitamin D3.

The nano-carrier topical composition with Vitamin D3 includes water. Water may be used to enhance penetration of the composition in the skin. Hydration of the stratum corneum may increase the penetration of both hydrophilic and hydrophobic drugs. Water suitable for the present composition may be potable water. The water may be deionized, filtered, distilled, or tap water from the spigot.

The nano-carrier topical composition with Vitamin D3 may be formulated for topical administration as a niosomal gel. Proniosomes are dry, free flowing granular products which upon hydration form multi lamellar niosome dispersions. Niosomes are non-ionic, surfactant-based vesicles, generally formed by mixing a non-ionic surfactant with an excipient, such as cholesterol.

Proniosomes may be prepared by any known method, including but not limited to the slurry method, the coacervation phase separation method, or the spray coating method. In the slurry method, proniosomes are produced using maltodextrin as a carrier. A surfactant is added to maltodextrin powder in a rotary evaporator and a vacuum is applied until the resulting powder appears to be dry and free flowing. In the coacervation phase separation method precise amounts of surfactant, lipid, and drug are mixed with an alcohol, warmed, mixed, and warmed again at 60-70° C. until the surfactant is dissolved, followed by the addition of 0.1% v/v glycerol solution, resulting in the formation of proniosomes upon cooling. In the spray coating method surfactant in an organic solvent is sprayed into sorbitol powder and the solvent is evaporated. This process may be repeated until a desired surfactant load is reached.

Hydration of proniosomes to form niosomes may be achieved by adding an aqueous solution containing Vitamin D3 to the proniosomes and briefly agitating the mixture at 80° C. for a few minutes to obtain a niosomal suspension.

Thus, the nano-carrier topical composition of Vitamin D3 may include niosomes or any other suitable nano-carrier. Other nano-carriers known in the art, include, for example, liposomes, polymersomes, micelles, and polymer-based vesicles. The use of a nano-carrier may assist the nano-carrier topical composition of Vitamin D3 in penetrating the skin and delivering Vitamin D3 to the tissues. The nano-carriers can have an average diameter of about 50.8 μm, The nano-carrier topical composition with Vitamin D3 may be made by mixing Span 40, Span 80, cholesterol, and an amorphous powder of Vitamin D3 in 70% ethanol to form a mixture. The mixture may be mixed evenly while heating in order to ensure that the surfactants (Span 40 and Span 80) are completely dissolved. Water may be added to the mixture, and the mixture may be heated to about 60-70° C. to form a liquid gel. The liquid gel may be stored in a dark place at room temperature for at least a day. Aloe vera gel, 0.1% glycerin, almond oil, and sufficient NaOH to bring the liquid gel to an alkaline pH may then be added to form a liquid gel dispersion. Optionally, a perfume may be added at this stage in order to provide the liquid gel dispersion with a pleasing scent. During the process of mixing, other inactive ingredients may be added. Suitable inactive ingredients that may be added include, but are not limited to preservatives, such as carbomer 940, Methyl Paraben, and Triethylamine.

The composition may deliver 5000 IU of Vitamin D3 in 1 ml (gram) of gel. Daily application of the nano-carrier topical composition with Vitamin D3 to the skin was found to return the 25OHD level to a minimum normal level of 30 ng/mL within a 90-day period. Accordingly, Vitamin D3 may safely be delivered through the dermal route.

In an embodiment, the nano-carrier topical composition with Vitamin D3 may be made by mixing about 7.5 g Span™ 40, about 7.5 g Span™ 80, about 3.5 g cholesterol, and about 6 g of an amorphous powder of Vitamin D3 in about 10 ml 70% Ethanol to form a mixture. The mixture may be mixed evenly while heating for about 10 minutes in order to ensure that the surfactants (Span™40 and Span™80) are completed dissolved. About 10 ml of water may be added to the mixture, and the mixture may be heated for about 6 minutes to about 60-70° C. to form a liquid gel. The liquid gel may be stored in a dark place at room temperature for at least about 24 hours. About 8 ml Aloe vera gel, about 2 ml 0.1% glycerin, about 3.5 ml 100% almond oil, about 1 ml perfume, and sufficient NaOH to bring the liquid gel to an alkaline pH (up to about 2 ml) may then be added to form a liquid gel dispersion. The liquid gel dispersion can be cooled to room temperature to form a niosomal gel.

As discussed above, nano-carrier topical administration of the topical composition with Vitamin D3 may allow Vitamin D3 to pass into the body's systemic circulation. As such, the topical composition with Vitamin D3 may be useful for treating bone diseases for which Vitamin D supplementation is essential, such as osteopenia, osteoporosis, rickets, and osteomalacia.

Transdermal administration of Vitamin D3, as described herein, may be particularly desirable for the elderly, for children who require vitamin D supplementation, and in patients requiring Vitamin D3 supplementation who already have a large medication burden.

The following example is illustrative only, and is not intended to limit the present teachings.

EXAMPLE

A study was carried out on 150 patients with low vitamin D. Patients were between 18 and 80 years of age and gave written consent for participation. The patients were divided into three groups, a group treated with TopD3 synthesized according to the methods of U.S. Pat. No. 9,707,243 (Group A), a group treated with Improved TopD3 (Group B), and a group treated with a placebo (Group C). The study was double-blind, as neither the investigators nor the patients were aware of which group any individual patient was assigned to. Patients applied 1 ml of the gel (TopD3, TopD3-I, or Placebo) as a metered dose for 90 days.

Patients underwent physical examinations and laboratory tests (Bone Profile), including tests to assess Calcium, Phosphorous, 25OHD level and paranthormone levels. Patients were selected based upon 25OHD levels and, if selected, were allowed to pick one of 150 envelopes containing a gel, patients immediately started applying 1 ml of the gel for 3 months. Patients were followed up after the first, second, and third months, and the blood tests were repeated. At each visit, adverse events were also recorded.

TopD3 used in this experiment was synthesized according to U.S. Pat. No. 9,707,243, and contained about 5% Vitamin D3, 5% aromatic oil, 10% glycerin, about 10% of a preservative, and 70% aloe vera gel.

TopD3-I used in this experiment was synthesized according to the methods discussed herein and contained Span™ 40, Span™ 80, cholesterol, Almond Oil, Glycerin, Ethanol, Aloe Vera gel, 5,000 IU/ml cholecalciferol, and Sodium Hydroxide (NaOH).

Both TopD3 and TopD3-I were synthesized as micellar compositions, with TopD3 micelles having an average diameter of 312.7 um and TopD3-I micelles having an average diameter of 50.8 um.

Figure 2:
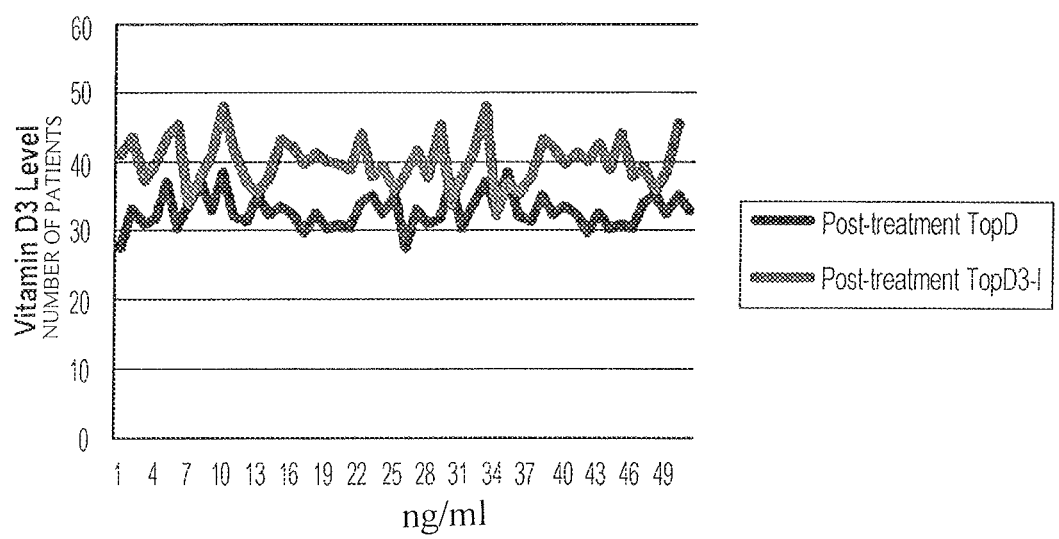
FIG. 2 depicts a graph comparing the post-treatment vitamin D3 levels of patients allocated to the TopD3 group (Group A) and patients allocated to the TopD3-I group (Group B).
Figure 3:
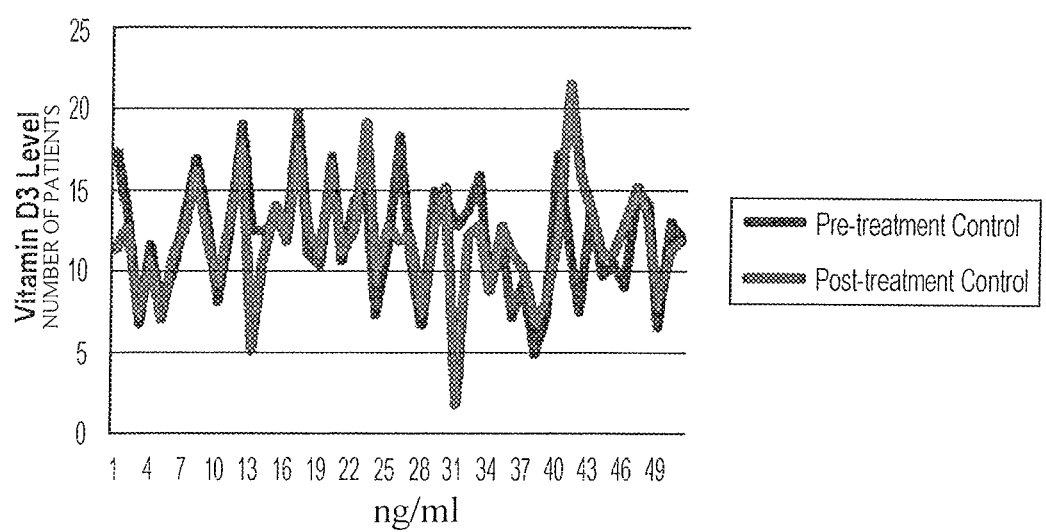
FIG. 3 depicts a graph comparing the pre-treatment and post-treatment vitamin D3 levels of patients allocated to the Control group (Group C).

The average age of the patients in each of the groups was 58.9±11.7 years, 57.6±13.78 years, and 57.1±10.6 years in groups A, B and C respectively. The pre-treatment 25OHD level in Group A was 11.64±5.1 (2-12) ng/ml. The pre-treatment 25OHD level in Group B was 11.04±3.9 (3-15). The pre-treatment 25OHD level in Group C was 12.1±6.8 (3-12) ng/ml. Post treatment the levels were: Group A 32.92±4.9 (12-39) ng/ml, Group B 41.6±6.04 (29-54), and Group C 11.95±5.9 (2-19) ng/ml (p<0.001). These results are summarized in Table 1. The pretreatment and posttreatment Vitamin D3 levels in Groups A, B, and C are also compared in FIGS. 1-3.

TABLE 1

Demographic and Vitamin D3 Data

| | Age (Years) | Vitamin D3 Pre-Treatment ng/ml | Vitamin D3 Post-Treatment ng/ml |
|---|---|---|---|
| TopD3 Group A | 589 ± 11.7 | 11.64 ± 5.1 | 32.92 ± 4.9 |
| TopD3-I Group B | 57.6 ± 13.78 | 11.04 ± 3.9 | 40.1 ± 3.54 |
| Control Group C | 57.1 ± 10.6 | 12.1 ± 6.8 | 11.95 ± 5.9 |

In Group A, 5 patients (10%) showed levels of Vitamin D3 that did not improve in response to treatment and 7 patients (14%) had local irritation of the skin, which subsided. In Group B all patients crossed the normal serum vitamin D level of ≥30 ng/ml. There were no adverse reactions reported in Groups B or C.

In conclusion, the results of this study demonstrate that TopD3-I is more efficacious than TopD3, that TopD3-I is safe, and that the levels of Vitamin D3 resulting from TopD3-I administration were significantly higher post treatment (p<0.0001) than the levels found in the TopD3 and control groups.

It is to be understood that the system and method for doing something is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A nano-carrier topical composition formulated for delivering Vitamin D3 transdermally to a patient suffering from a bone-condition, consisting essentially of a mixture of:
- about 6 g of Vitamin D3;
- about 7.5 g of sorbitan monopalmitate;
- about 7.5 g of sorbitan monooleate;
- about 3.5 g of cholesterol;
- about 10 ml ethanol;
- about 3.5 ml almond oil;
- about 2 ml 0.1% v/v glycerin;
- about 10 ml water;
- up to 2 ml sodium hydroxide, wherein the sodium hydroxide is sufficient to bring the composition to an alkaline pH; and
- about 8 ml aloe vera gel.

2. A nano-carrier topical composition formulated for delivering Vitamin D3 transdermally to a patient suffering from a bone-condition, consisting essentially of a mixture of:
- about 6 g of Vitamin D3;
- about 7.5 g of sorbitan monopalmitate;
- about 7.5 g of sorbitan monooleate;
- about 3.5 g of cholesterol;
- about 10 ml ethanol;
- about 3.5 ml almond oil;
- about 2 ml 0.1% v/v glycerin;
- about 10 ml water;
- up to 2 ml sodium hydroxide, wherein the sodium hydroxide is sufficient to bring the composition to an alkaline pH;
- about 8 ml aloe vera gel; and
- either a perfume or a preservative.

3. The nano-carrier topical composition with Vitamin D3 according to claim 1, wherein the nano-carriers have an average diameter of 50.8 μm.

4. The nano-carrier topical composition with Vitamin D3 according to claim 3, wherein the nano-carriers are niosomes.

5. The nano-carrier topical composition with Vitamin D3 according to claim 2, wherein the preservative is selected from the group consisting of carbomer 940, methyl paraben, and EDTA.

6. A method of transdermally treating a bone-condition characterized by Vitamin D deficiency, comprising the step of topically applying to the skin an effective amount of a composition having a mixture consisting essentially of:
- about 6 g of Vitamin D3;
- about 7.5 g of sorbitan monopalmitate;
- about 7.5 g of sorbitan monooleate;
- about 3.5 g of cholesterol;
- about 10 ml ethanol;
- about 3.5 ml almond oil;
- about 2 ml 0.1% v/v glycerin;
- about 10 ml water;
- up to 2 ml sodium hydroxide, wherein the sodium hydroxide is sufficient to bring the composition to an alkaline pH; and
- about 8 ml aloe vera gel.

7. The method of treating a condition according to claim 6, wherein the condition is selected from the group consisting of osteopenia, osteoporosis, rickets, and osteomalacia.

8. The method of treating a condition according to claim 6, wherein the effective amount includes 5000 IU per diem Vitamin D3.

9. The nano-carrier topical composition with Vitamin D3 according to claim 2, wherein the nano-carriers have an average diameter of 50.8 μm.

10. The nano-carrier topical composition with Vitamin D3 according to claim 9, wherein the nano-carriers are niosomes.

* * * * *